(12) United States Patent
Maas et al.

(10) Patent No.: US 11,513,068 B2
(45) Date of Patent: Nov. 29, 2022

(54) METHOD AND APPARATUS FOR DETECTING A PULSED THZ BEAM WITH TIME OF FLIGHT CORRECTION

(71) Applicant: ABB Schweiz AG, Baden (CH)

(72) Inventors: Deran Maas, Zurich (CH); Branimir Radisavljevic, Zurich (CH); Mariya Porus, Dietikon (CH); Jacobus Lodevicus Martinus Van Mechelen, Regensdorf (CH)

(73) Assignee: ABB Schweiz AG, Baden (CH)

( * ) Notice: Subject to any disclaimer, the term of this patent is extended or adjusted under 35 U.S.C. 154(b) by 295 days.

(21) Appl. No.: 16/846,892

(22) Filed: Apr. 13, 2020

(65) Prior Publication Data

US 2020/0240909 A1 Jul. 30, 2020

Related U.S. Application Data

(63) Continuation of application No. PCT/EP2018/078039, filed on Oct. 15, 2018.

(30) Foreign Application Priority Data

Oct. 13, 2017 (EP) .................................... 17196406

(51) Int. Cl.
*G01N 21/3586* (2014.01)
*G01N 33/32* (2006.01)

(52) U.S. Cl.
CPC ......... *G01N 21/3586* (2013.01); *G01N 33/32* (2013.01); *G01N 2201/0697* (2013.01); *G01N 2201/06113* (2013.01)

(58) Field of Classification Search
CPC ............... G01N 21/3586; G01N 33/32; G01N 2201/06113; G01N 2201/0697
See application file for complete search history.

(56) References Cited

U.S. PATENT DOCUMENTS

| 8,638,443 | B2 | 1/2014 | Haran et al. |
| 2010/0280779 | A1 | 11/2010 | White et al. |

(Continued)

FOREIGN PATENT DOCUMENTS

| EP | 2085765 A1 | 8/2009 |
| EP | 2899498 A1 | 7/2015 |

(Continued)

OTHER PUBLICATIONS

Gregory et al., "Extending terahertz paint thickness measurements to advanced industry-standard automotive paint structures," *2016 41st International Conference on Infrared, Millimeter, and Terahertz waves* (IRMMW-THz), IEEE, 2 pp. (Sep. 25, 2016).

(Continued)

*Primary Examiner* — David P Porta
*Assistant Examiner* — Fani Polyzos Boosalis
(74) *Attorney, Agent, or Firm* — Leydig, Voit & Mayer, Ltd.

(57) ABSTRACT

A method and apparatus for detecting a pulsed THz beam includes emitting, by THz emitter, pulsed THz radiation of outgoing pulse shape for interacting with target body; detecting, by THz detector, incoming THz radiation comprising THz pulses, and outputting, by THz detector, a raw detector data of pulse shapes of incoming THz pulses; and determining, by pulse shape reconstruction module, a reconstructed incoming pulse shape based on the raw detector data, measuring, by sensor, a time-of-flight quantity (d) affecting the time of flight of the THz radiation; and adjusting operation of at least one of THz emitter, THz detector and pulse shape reconstruction module using the time-of-flight quantity (d), for correcting for variations in time of flight of the THz radiation.

16 Claims, 5 Drawing Sheets

(56) References Cited

U.S. PATENT DOCUMENTS

2015/0090881 A1* 4/2015 King ............... G01N 21/3586
206/564
2017/0023469 A1 1/2017 Zimdars et al.

FOREIGN PATENT DOCUMENTS

EP          2899499 A1    7/2015
WO    WO 2016/138935 A1    9/2016

OTHER PUBLICATIONS

Su et al., "Terahertz sensor for non-contact thickness and quality measurement of automobile paints of varying complexity," *IEEE Transactions on Terahertz Science and Technology*, 4(4): 432-439 (Jul. 2014).
European Patent Office, International Search Report in International Patent Application No. PCT/EP2018/078039.
European Patent Office, Written Opinion in International Patent Application No. PCT/EP2018/078039, 10 pp. (dated Nov. 16, 2018).
European Patent Office, Extended European Search Report in European Patent Application No. 17196406.7, 11 pp. (dated Feb. 9, 2018).

* cited by examiner

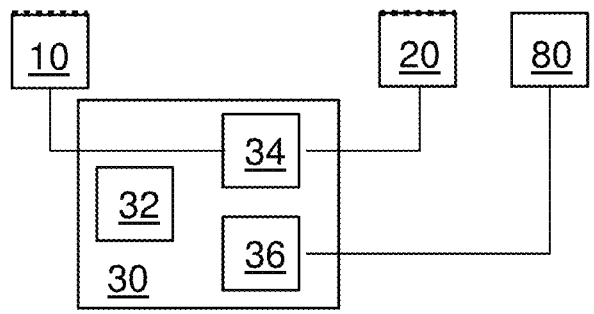
FIG. 3
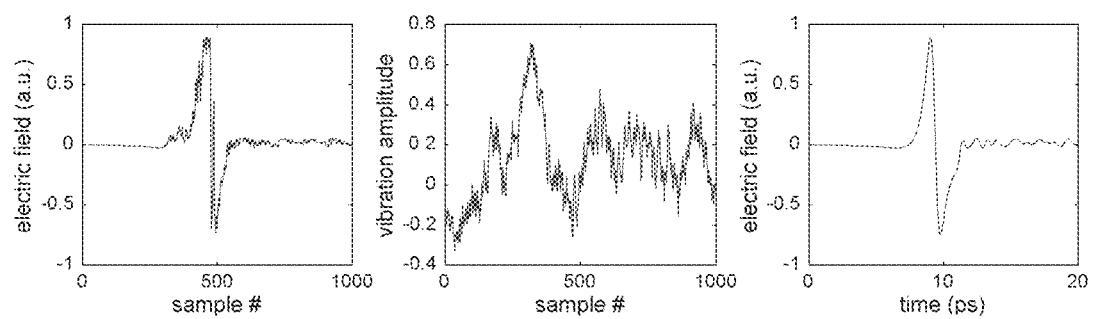
FIG. 8a  FIG. 8b  FIG. 8c

METHOD AND APPARATUS FOR DETECTING A PULSED THZ BEAM WITH TIME OF FLIGHT CORRECTION

CROSS-REFERENCE TO RELATED APPLICATIONS

This patent application is a continuation of co-pending International Patent Application No. PCT/EP2018/078039, filed Oct. 15, 2018, which claims the benefit of European Patent Application No. 17196406.7, filed Oct. 13, 2017, which applications are hereby incorporated herein by this reference for all purposes.

FIELD OF THE DISCLOSURE

Aspects of the invention relate to a method of detecting a pulsed THz beam, wherein THz radiation is emitted by a THz emitter, travels to a target body to be inspected, interacts with the target body, travels to a THz detector, and is detected by the THz detector in time domain, e.g. for material inspection. Other aspects of the invention relate to a coating method for coating a body, and to a corresponding apparatus and coating facility.

TECHNICAL BACKGROUND

Methods based on THz radiation have been proposed for various purposes such as materials testing and quality control applications. For example, JP 2004028618 A and EP 2213977 A1 describe respective methods for determining the thickness of a paint film using THz radiation.

In particular, THz time-domain spectroscopy is promising for early and automatized quality control of coatings, e.g., paint films of painted car bodies during production, in a contactless manner. For example, EP 2899499 A1 describes a sensor system for characterizing a coating by THz radiation. The system has a THz emitter directing an outgoing THz radiation towards a coated body (target body), and a THz detector for detecting incoming THz radiation having interacted with the coated body. The system is capable of characterizing the coating by analyzing the change of the incoming THz radiation waveform to the outgoing THz radiation waveform.

For this purpose, it is crucial to determine the waveform of the incoming THz radiation with high accuracy. This is typically achieved by the following setup: The THz emitter emits the outgoing THz radiation as a short THz signal pulse in a repeated manner, and the THz detector has a switchable antenna that can be activated on time scales that are sufficiently short for resolving details of the incoming THz signal pulse.

For example, to detect THz pulses with sub-picosecond resolution, micron-scale photoconductive dipole antennae with very short carrier lifetime of 1 ps or less are available. The antennae can be activated by an ultrashort laser pulse. The short recombination time of the semiconductor causes the gap resistance to change from nearly insulating to conducting (closing the switch) upon irradiation, and then back to insulating (opening the switch) on a picosecond time scale. Thus, each activation is analogous to closing a switch, which allows the antenna gap to conduct for a sub-picosecond instant and to measure the electric field (corresponding to one locus of the waveform) at that instant. The measurement is repeated many times while a delay time for activation of the THz detector's switchable antenna is varied. The repeated measurements then allow reconstruction of the waveform of the incoming THz signal pulse.

The above measurement strategy is illustrated in FIGS. 4a and 4b. FIG. 4a shows the waveform 66 (detectable electric field component as function of time) of the incoming THz signal pulse. The waveform 66 is received periodically at the THz detector; and for each repetition of the THz pulse, the THz detector's antenna is activated at a different time offset t1, . . . , t6, and measures the waveform at that time offset, as indicated by the small circles on top of the waveform 66. For the sake of simplicity of explanation, the switching of the THz detector's antenna is assumed to be instantaneous, with an infinitesimally small time resolution.

In reality the switching will extend over a certain time span. The simplified discussion of instantaneous switching is purely for the sake of ease of understanding. THz detectors having other switching characteristics can be analyzed in an analogous manner by reverse convolution, as described, for example, in R. Alan Cheville, "Terahertz Time-Domain Spectroscopy with Photoconductive Antennas", in: Susan L. Dexheimer, Terahertz Spectroscopy, Boca Raton 2008. The invention encompasses THz detectors with any switching characteristics.

In FIG. 4a, each activation of the THz detector (each circle in FIG. 4a) belongs to a different one of the repeatedly received pulses. In the example shown in FIGS. 4a and 4b, the six measurements at time offsets t1, . . . , t6, may be obtained from six subsequent THz pulses. These six measurements, together with the known time offsets, map out the THz waveform in time and allow reconstruction of the incoming THz signal pulse waveform, as shown in FIG. 4b. The above discussion is simplified, and in reality much more than six measurements are performed, each extending over a certain time span, as discussed in more detail below.

The time offsets t1, . . . , t6 can for example be obtained by delaying a laser pulse that activates the THz detector with respect to a laser pulse that triggers the THz pulse, wherein both laser pulses may originate from the same pulsed laser with a tunable delay stage in the optical path towards the detector, or from two pulsed lasers whose pulse rates are slightly detuned relative to each other, such as in asynchronous optical sampling (ASOPS) and electronically controlled optical sampling (ECOPS) setups. Further details of measurement setups are described, for example, in R. Alan Cheville, cited above.

In many real-world applications, it has turned out that the measured THz signal has limited accuracy and reproducibility. However, the materials testing and quality control applications rely on tiny details of the THz signal and therefore require very high accuracy. An object of the present invention is to improve the accuracy and reproducibility of THz measurements in real-world applications.

SUMMARY OF THE INVENTION

In view of the above, according to an aspect of the invention, a method of detecting a pulsed THz beam according to claim 1 and an apparatus for detecting a pulsed THz beam according to claim 12 are provided. Further aspects and details are described below and in the dependent claims.

According to an aspect of the invention, the method of detecting a pulsed THz beam comprises: emitting, by a THz emitter, THz radiation comprising a time series of THz pulses having an outgoing pulse shape, so that the THz radiation travels along a first path from the THz emitter to a target body to be inspected, interacts with the target body, and travels along a second path from the target body to a THz detector; detecting, by the THz detector, the incoming THz radiation being a time series of incoming THz pulses, and outputting, by the THz detector, a raw detector data being a time series of data relating to an incoming pulse shape of the incoming THz pulses; and determining, by a pulse shape reconstruction module, a reconstructed incoming pulse shape of the incoming THz radiation based on the raw detector data.

The Apparatus according to any one of the apparatus claims may be adapted for the method according to any one of the method claims. Conversely, the method according to any one of the method claims may be carried out by the apparatus according to any one of the apparatus claims.

The inventors have found out that one source of errors limiting accuracy and reproducibility are disturbances that occur in the context of an industrial environment. As a consequence, the distance (more precisely, the time of flight) along the first path (from the THz emitter to the target body) and/or along the second path (from the target body to the THz detector) is not constant during the measurement but has variations. These disturbances can for example be caused by vibrations of the THz emitter, the THz receiver, and/or the target body. The disturbances can also be caused by a humidity change of the ambient air, given that this decreases the speed of light. In an industrial environment, it is difficult to diminish or eliminate these disturbances.

According to an aspect of the invention, a sensor is provided which measures a time-of-flight quantity affecting the time of flight of the THz radiation along at least one of the first path and the second path. The time-of-flight quantity is measured in a time-dependent manner while the THz radiation is emitted by the THz emitter. Using this time-of-flight quantity, the operation of at least one of the THz emitter, the THz detector and the pulse shape reconstruction module can then be adjusted for correcting for a variation in the time of flight of the THz radiation. Here, the time-of-flight quantity does not need to be the signal directly measured by the sensor, but may be a derived quantity, obtained from the signal measured by the sensor.

Thereby, embodiments of the invention open ways to accurately and reliably measure THz radiation even in an industrial environment in the presence of disturbances. Examples of disturbances are vibrations, other motion, and other variations in the environment having an influence on the time of flight of the THz radiation.

The more accurate and reliable THz measurements enable a more accurate and reliable characterization of the target body. Thereby, for example, a more accurate and reliable quality control is enabled.

Further advantages, features, aspects and details that can be combined with embodiments described herein are evident from the dependent claims, the description and the drawings.

BRIEF DESCRIPTION OF THE FIGURES

The details will be described in the following with reference to the figures, wherein

FIG. 3 is a schematic view of a detection apparatus according to an embodiment of the invention;

FIG. 8a is a diagram showing a reconstructed THz pulse shape obtained from a vibrating object by the method known in the art;

FIG. 8b is a diagram showing the vibration amplitude of the vibrating object;

FIG. 8c is a diagram showing a reconstructed THz pulse shape obtained from a vibrating object by the method according to an embodiment of the invention;

DETAILED DESCRIPTION OF THE FIGURES AND OF EMBODIMENTS

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

Figure 1:
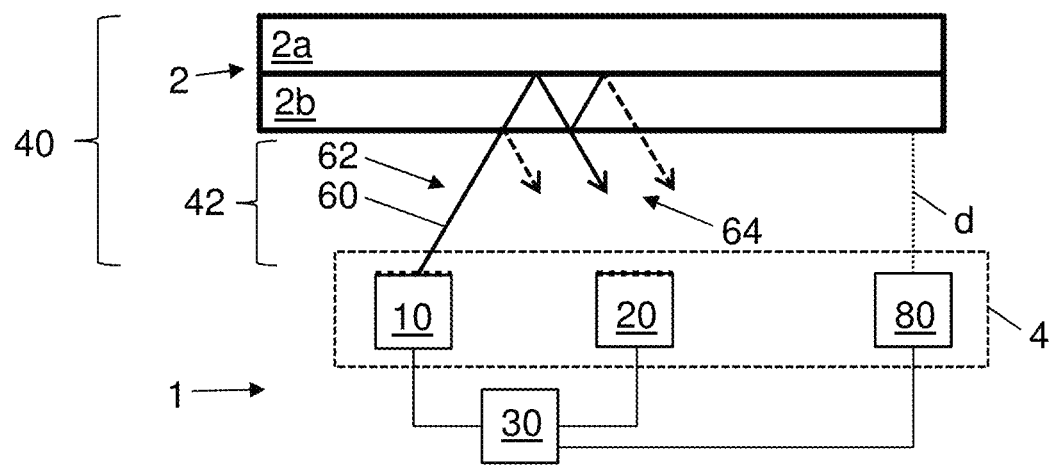
FIG. 1 is a schematic view illustrating the operation of a detection apparatus according to an embodiment of the invention.
Figure 2:
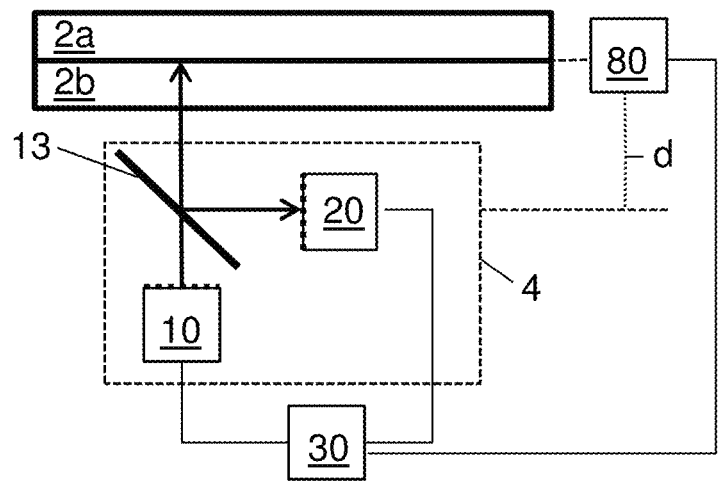
FIG. 2 is a schematic view illustrating the operation of a detection apparatus according to a further embodiment of the invention.

With reference to FIGS. 1-3, embodiments of the detection apparatus are now described.

FIG. 1 is a schematic side view illustrating basic components and general operation of a detection apparatus 1 according to an embodiment of the invention. The detection apparatus 1 has a detection head 4 with a THz emitter 10 for emitting THz radiation, a THz detector 20 for detecting THz radiation, and a sensor 80. The detection head 4 mechanically couples the THz emitter 10, the THz detector 20 and the sensor 80 mechanically to each other.

The detection apparatus 1 further has a processing unit 30 operationally coupled to the THz emitter 10, the THz detector 20 and the sensor 80. Herein, "operationally coupled" includes an interface of the processing unit coupled to the respective system, e.g., to the THz emitter 10 and to the THz detector 20 for triggering emission of THz radiation and activation of the THz detector (as described above with respect to FIG. 4a), respectively, at predetermined timings. The processing unit 30 further has an interface to the THz detector 20 and to the sensor 80 for receiving (raw) measurement data indicative of the response signal and sensor data, respectively.

The processing unit 30 is shown in more detail in FIG. 3. The processing unit 30 is equipped with a processor 32 and with a memory in which software code is stored enabling the processor to carry out any method described herein. The processing unit 30 has a detector/emitter control unit 34 operationally coupled to the THz emitter 10 and to the THz detector 20 for generating a periodic sequence of THz pulses by the THz detector 20, and for activating the THz detector at time offsets with respect to the generated THz pulses, for detecting incoming THz pulse portions (raw detector data) at these time offsets (e.g., by periodically directing optical laser pulses to the THz emitter 10 and the THz detector 20). The detector/emitter control unit 34 is further operationally coupled to the THz detector 20 for receiving and processing a detected response signal representing the detected THz radiation. The processing unit 30 further has a pulse shape reconstruction module 36 operationally coupled to the sensor 80 for receiving a time-of-flight quantity (e.g., distance d) and for synchronizing the time-of-flight quantity with the raw detector data, and for determining a reconstructed incoming pulse shape of the incoming THz radiation based on the raw detector data. Further operation of the processing unit 30 and of its components is described below.

Further optional details of the THz emitter 10 and the THz receiver are not shown in FIG. 1, such as a THz optical system such as lens(es) and/or mirror(s).

Further, FIG. 1 shows a coated body (target body) 2. The detection apparatus 1 is arranged such that the coated body 2 is faced by the THz emitter 10 and the THz detector 20, with an air gap 42 between the emitter and THz detectors 10, 20 on the one side and the coated body 2 on the other side.

In the embodiment of FIG. 1, the coated body 2 has a substrate 2a and a paint coating 2b, but the invention is not limited to paint coatings but can be applied to any other coatings as well. Further, in FIG. 1, the paint coating 2b has one layer. The paint coating 2b may alternatively be a paint stack having more than one layer, e.g. two or three or four layers. According to a preferred aspect, the described method and system is available for a multi-layered coating having at least two layers.

The sensor 80 is a distance sensor for measuring the distance d to the coated body 2. Thereby, the sensor 80 is adapted for measuring a motion (e.g., vibrations) of the coated body 2 relative to the detector head 4.

Next, operation of the apparatus 1 of FIG. 1 is described. The THz emitter 10 emits THz radiation 60 comprising a time series of THz pulses having a predetermined pulse shape (outgoing pulse shape).

The emitted THz radiation 60 (solid line) travels along a first path 62 from the THz emitter 10 to the coated body 2, traversing the air gap 42, whereupon the THz radiation interacts with the coated body 2. A portion of the THz radiation, indicated by the solid line in FIG. 1, is reflected at the surface of substrate 2a and propagates back through the air gap 42 and towards the THz detector 20. Other portions of the radiation signal 60, indicated by the dashed lines in FIG. 1, are partially reflected at various layer interfaces of the coated body (more precisely, they are (almost fully) reflected at the substrate side and partially reflected at the air side of the coating 2b). Besides these reflections, also the propagation speed of the various portions of the THz radiation is influenced during their interaction with the coated body 2. In short, the THz radiation interacts with the coated body 2 in a manner that depends on the structure and properties of the coated body 2.

After this interaction, the THz radiation travels along a second path 64 from the target body 2 to the THz detector 20 (as incoming THz radiation). The THz detector 20 detects the incoming THz radiation, so that the pulse shape of the incoming THz radiation is obtained (more details below).

The pulse shape of the incoming THz radiation 64 carries detailed information about the paint coating 2b of the coated body 2 (e.g., thickness and optical material properties), due to the interaction with the coating, in particular due to the multiple reflections illustrated in FIG. 1. This information is contained in the pulse shape of the incoming THz pulse 64 (together with the reference pulse shape of the emitted THz signal 60), e.g., in terms of characteristic features due to the reflection at distinct interfaces of the stack. The information—the thickness d and other properties of the coating 2b—can therefore be deduced by analysis of the pulse shape. Methods for determining these parameters are described, for example, in EP 2899498 A1 or in WO 2016/138935 A1, which are fully incorporated by reference herein.

For obtaining the thickness d and other optical material properties of the coated body 2 and its coating layers, the pulse shape of the incoming THz radiation should be known to very high accuracy. Therefore, next, the method of determining the pulse shape of the incoming THz radiation by the pulse shape reconstruction module according to an embodiment of the invention is described.

Generally, the real-time measurement of the THz radiation is performed as described above with respect to FIGS. 4a and 4b, except for the differences mentioned in the following. Thus, the THz emitter 10 is triggered to emit a THz pulse of a given (outgoing) waveform periodically, and therefore, after interaction with the coated body, an incoming waveform 66 is received periodically at the THz detector 20. For each repetition of the incoming THz pulse, the THz detector is activated at a different time offset t1, . . . , t6, and measures the waveform at that time offset, as indicated by the small circles on top of the waveform 66 in FIGS. 4a and 4b. Thus, each activation of the THz detector (each circle shown in FIGS. 4a and 4b) belongs to a different one of the repeatedly received pulses.

Figure 4A:
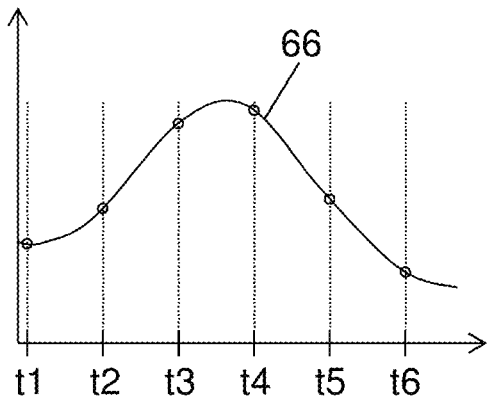
FIG. 4a, 4b are diagrams illustrating a method for reconstructing the pulse shape of measured THz radiation in time domain known in the art.
Figure 4B:
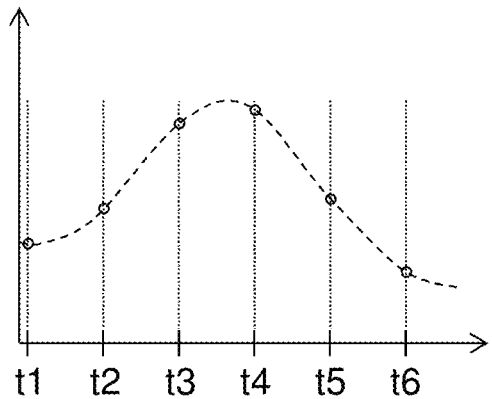

However, the sensing technology of FIGS. 4a and 4b, if applied in the context of an industrial environment, is sometimes inaccurate. The inventors found that a source of inaccuracies is that the distance between the THz detection head 4 and the coated body 2 may not be constant during the measurement, resulting in a varying time of flight of the THz beam from pulse to pulse. This variation in distance can, for instance, be caused by vibrations related to the detection head 4 or the coated body 2. Also, the time of flight of the THz beam can vary, for example, due to a humidity change of the ambient air. In an industrial environment, it is sometimes not technically or economically feasible to diminish or eliminate these perturbations.

Figure 5A:
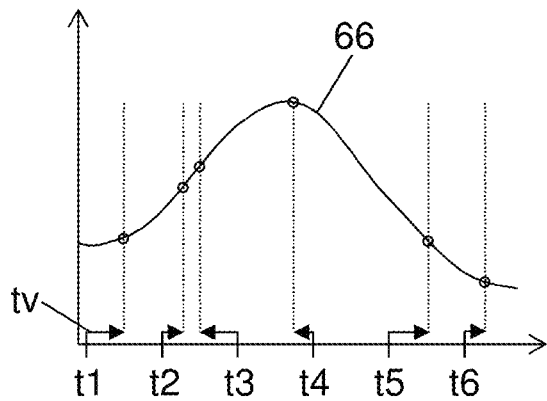
FIG. 5a, 5b are diagrams illustrating the shortcomings of the method for FIGS. 4a, 5b in the presence of disturbances.
Figure 5B:
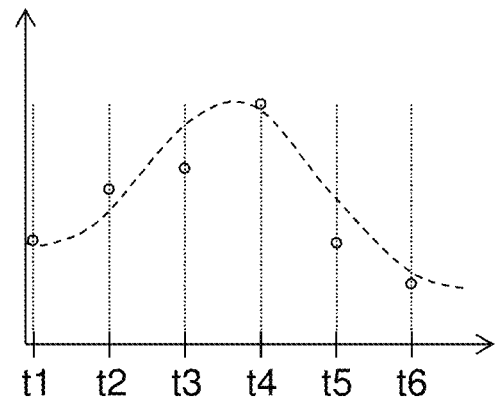

FIGS. 5a and 5b illustrate how variations in the time of flight can diminish reliability and accuracy of the measurement in the setup of FIGS. 4a and 4b. FIG. 5a again illustrates a real-time measurement of an incoming THz pulse (solid line: time-dependent electric field E at the detector as a function of time), wherein the measurement is performed by activating the detector at six different times t1, . . . , t6 for six subsequent functions. Here, in FIG. 5a, each of the six incoming THz pulses arrives at the THz detector with a random time-of-flight variation tv due to the random variation in time of flight. In FIG. 5a, this is not shown as a relative horizontal shift of the six THz pulses (solid curve), but instead the "zero" time of FIG. 5a is offset by the respective time-of-flight variation tv for each of the six pulses, such that all the six incoming THz pulses are represented by the same solid line of FIG. 5. In other words, relative to a time of emitting the pulse at the THz emitter, the time variables of FIG. 5a are shifted, for each of the six measurements (solid circles), by respective times (−tv) corresponding to the respective THz pulse at which the measurement is performed. Correspondingly, in FIG. 5 the times t1, . . . , t6 of activating the detector (which are triggered relative to the emitted THz pulse) are shifted by the time-of-flight variation tv.

In the known method, this shift is not accounted for during reconstruction of the THz pulse shape, but it is instead assumed that the measurements took place at times t1, . . . , t6 as shown in FIG. 5b. Thereby, the accuracy and reliability of the pulse shape reconstruction is greatly diminished.

Figure 6A:
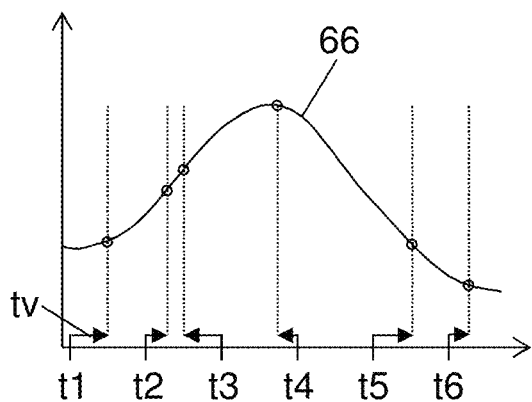
FIG. 6a, 6b are diagrams illustrating a method for reconstructing the pulse shape of measured THz radiation in time domain according to an embodiment of the invention.
Figure 6B:
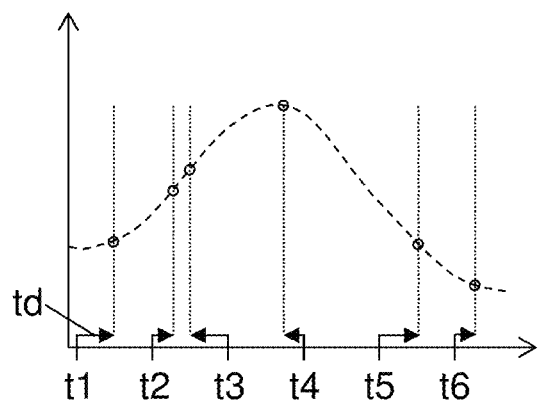

FIGS. 6a and 6b show a step of measuring and reconstructing the THz pulse shape by a pulse shape reconstruction module according to an embodiment of the invention. Therein, the THz detector is activated at predetermined offset times t1, . . . , t6, relative to the emitted THz pulse, as in the known method. The offset times t1, . . . , t6 can be set, for example, by an optical delay stage delaying the laser pulse used for activating the THz receiver, by the ASOPS or ECOPS methods, or by any other known method. In addition, the time-of-flight variation tv is determined, for example, by any of the methods described herein.

For reconstructing the THz pulse shape, respective correction times td are added to the offset times t1, . . . , t6. The correction times td are equal to the time-of-flight variation tv shown in FIG. 6a (up to a constant global offset). Thereby, the error (see FIG. 5b) due to the variation in the time of flight of the THz radiation is corrected. Thus, as shown in FIG. 6b, it becomes possible to reconstruct the incoming pulse shape of the incoming THz radiation reliably and accurately.

Accordingly, the pulse shape reconstruction module operates as follows:

The raw detector data (electric field as a function of delay time t1, . . . , t6 with respect to the THz pulse emitted by the THz emitter) is received from the THz detector;

The time-of-flight variation tv, for each raw detector data measurement (e.g., for each THz pulse), is received from the sensor (the time-of-flight variation tv may, e.g., be calculated from a time-of-flight quantity d received from the sensor);

A corrected delay time is obtained by adding a correction time td to the delay time t1, . . . , t6, the correction time being equal to the time-of-flight variation tv (see FIG. 6b); and The reconstructed incoming pulse shape of the incoming THz radiation (dashed line in FIG. 6b) is determined based on the raw detector data (circles) and the corrected delay time.

The correction times td are obtained, in the embodiment of FIG. 1, as follows: The sensor 80 continuously measures the distance (time-of-flight quantity) d between the THz receiver head 4 and the body 2. From the distance d, the time of flight of the THz radiation 60 along the first path 62 and the second path 64 is obtained. Specifically, the respective time of flight of each of the THz pulses is obtained by synchronizing the time-of-flight quantity measurement with the measurements of the THz detector. The time of flight is then used, by the pulse shape reconstruction module, as the correction time td in the method illustrated in FIG. 6b, for correcting for the variation in the time of flight as described above. Herein, instead of the total time of flight, it is sufficient to calculate variations in time of flight, i.e., irrespective of a constant offset.

FIG. 8a shows a reconstructed real-time pulse shape of an incoming THz pulse having interacted with a vibrating body, obtained according to the illustrative method shown in FIGS. 5a and 5b. The pulse shape contains many non-reproducible jitters indicating that the measurement of the pulse shape is less accurate and less reliable. Due to these jitters, the optical material properties and thicknesses derived therefrom can be determined less accurately. FIG. 8b shows the vibration amplitude of the body obtained using a sensor 80 as illustrated in FIG. 1. FIG. 8c shows the reconstructed real-time pulse shape of the incoming THz pulse, obtained according to the method according to the embodiment shown in FIGS. 6a and 6b. The pulse shape is much more accurate and reliable, and is useful for extracting further information therefrom.

Figure 7A:
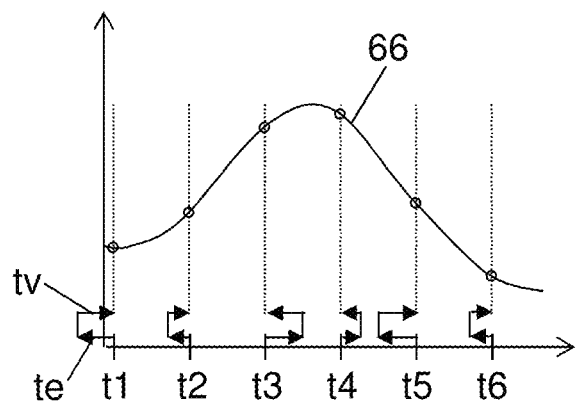
FIG. 7a, 7b are diagrams illustrating a method for reconstructing the pulse shape of measured THz radiation in time domain according to a further embodiment of the invention.

The embodiment can be varied in a number of manners to obtain further embodiments. For example, in the embodiment of FIGS. 7a and 7b, the offset times t1, . . . , t6 for activating the THz detector relative to the time of emitting the THz pulse are shifted by a correction time te for compensating the variation in time of flight tv shown in FIGS. 5a and 7a. Specifically, te is the negative of tv up to a constant offset.

This compensation may be achieved, for example, by adjusting the operation of the THz emitter, more specifically by offsetting the emission time of the emitted THz pulses by the correction time te, while not adjusting operation of the THz detector. This solution is possible, for example, in a method in which the THz emitted and the THz detector are triggered by two independent triggers (such as in the ASOPS or ECOPS methods). Alternatively, this compensation may be achieved by adjusting the operation of the THz detector, specifically by adapting the detection time offsets t1, . . . , t6 by a correction time te=+tv (up to a constant), for compensating the variation in time of flight tv. This adjustment may be obtained by changing the trigger times in the ASOPS or ECOPS methods, or by adjusting the delay time of an optical delay stage for the laser pulse activating the THz detector. The delay time may, for example, be adjusted by adapting the length or the index of refraction of the optical delay stage.

More generally, the operation of the THz emitter and/or detector is adjusted such that the respective detection time offset for detecting a pulse portion of an incoming THz pulse, relative to the time of emitting the respective THz pulse, is shifted by the time of flight tv.

Figure 7B:
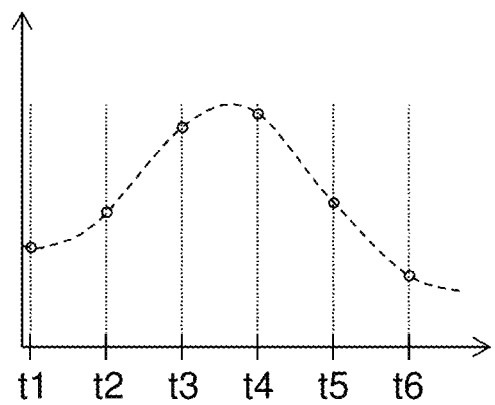

In summary, by the methods shown in FIGS. 6b and 7b, carried out by a pulse shape reconstruction module, the time-of-flight tv is synchronized with the raw detector data (i.e. the respective time of flight for each of the pulses corresponding to the times t1, . . . , t6 is obtained); the reconstructed incoming pulse shape of the incoming THz radiation is obtained based on the raw detector data (measurements indicated by circles). Further, in FIG. 6b, the operation of the pulse shape reconstruction module is adjusted using the correction time td (based on the time of flight tv), by adding tv to the offset times t1, . . . , t6, for correcting for a variation in the time of flight of the THz radiation. In FIG. 7b, the operation of the THz emitter or the THz detector is adjusted using the correction time te (based on the time of flight tv), by changing the relative time between triggering emission and detection of the THz pulse, for correcting for a variation in the time of flight of the THz radiation.

Next, various embodiments for obtaining the time of flight tv or related quantities (time-of-flight quantities) are discussed. Generally, a quantity that allows an estimate of the time of flight (and that is used for obtaining the time of flight or at least for correcting variations in time of flight) is referred to herein as the time-of-flight quantity.

One embodiment for obtaining the time of flight is shown in FIG. 1 described above. Here, the distance sensor d measures the distance between the THz detector head 4 and the coated body 2. This distance d is transmitted to the processing unit 30, and is used for calculating the length of the first and second path 62, 64 of the THz radiation and, consequently, the time of flight of the THz radiation. It is not necessary to measure the absolute distance d; it is sufficient to measure relative variations in the distance d and to calculate the variations in time of flight therefrom.

A further embodiment is shown in FIG. 2. Therein, contrary to FIG. 1, the sensor 80 is rigidly attached to the coated body 2. The sensor 80 is a distance sensor for measuring the distance d to the detector head 4. Thereby, like in FIG. 1, the sensor 80 is adapted for measuring a motion (e.g., vibrations) of the coated body 2 relative to the coated body 2.

The sensor 80 can include, for example, any of a triangulation laser distance sensor, a time-of-flight optical distance sensor (measuring the travel time of a laser signal or a THz pulse, for example), and a set of line segment sensors based on triangulation. Additionally or alternatively, the sensor 80 can also include an accelerometer used for determining distance variations.

In case of a distance sensor, the sensor 80 can be mounted on the THz detector head 4, the coated body 2 (including any part mechanically connected to these) or on a stationary element (e.g., a building wall or ceiling) for determining relative distance variations between the THz detector head 4 and the coated body 2. In case of an accelerometer, the sensor 80 can be mounted on THz detector head 4 or the coated body 2.

In a further embodiment, the sensor 80 can comprise a sensor for a further quantity influencing the time of flight, such as a humidity sensor. The humidity of the ambient air indirectly influences the time of flight due to its influence on the index of refraction. In this case the processing unit (the pulse shape reconstruction module) is adapted for calculating an estimated variation in time of flight from the humidity value measured by the humidity sensor. The humidity sensor may, for example, be realized by a THz pulse absorption evaluating unit for evaluating the absorptions of a THz pulse received by the THz detector or by a further THz detector. During propagation of the THz pulse, a portion of the pulse is absorbed by the humidity contained in the THz pulse's path. The absorption integrates over the humidity along the optical path and is therefore also useful when the humidity has a gradient in space. The THz pulse absorption evaluating unit may determine the integrated humidity by analysis of the detected THz pulse and the absorbed pulse portion due to the water absorption lines of the THz pulse. The relation between index of refraction (and therefore speed of light) and humidity is known or can be determined using a calibration run. From the integrated humidity and using this known relation, the THz pulse absorption evaluating unit then determines the variation of the time-of-flight quantity.

Also, in a further embodiment, a time-of-flight sensor for measuring the time of flight directly may be used as the sensor 80. The sensors 80 from the various embodiments may also be combined for obtaining a more robust estimate of the time of flight.

The embodiment of FIG. 2 also illustrates some further possible variants of the detection apparatus of FIG. 1. For example, in FIG. 2, in the detector head 4, the THz emitter 10 and the THz detector 20 are arranged with their (optical) axes at an angle (here: 90°), and the detector head 4 further comprises a beam splitter 13 arranged such as to co-align the axes. Thereby, the optical axes are co-aligned, so that the transmitted and received THz signals are collinear and normal to the surface of the coated body 2. Thereby, the main direction of propagation of the THz radiation preferably impinges normally on the coated body so that the transmitted and received THz signals are collinear and normal to the surface of the coated body 2.

Further alternative arrangements are possible. For example, the THz emitter 10 and the THz detector 20 may be arranged on opposite sides of the coated body 2, for enabling a transmission measurement instead of the measurement of the embodiment of FIG. 1.

Next, we describe a method of characterizing the coating 2b of the target body 2 (see FIGS. 1 and 2) by analyzing the reconstructed incoming THz pulse shape.

The processing section 30 (see FIG. 1) receives the incoming THz radiation and the pulse shape reconstruction module 36 provides a reconstructed incoming pulse shape of the incoming THz radiation as described above. The processing section 30 also receives, or has stored therein, the waveform 60 emitted by the emitter 10. The processing section 30 then performs an analysis of the response waveform (taking into account the original waveform and other information such as detected moisture and/or temperature), and thereby obtains the paint parameters by the method described herein (see e.g. EP 2899498 A1 or WO 2016/138935 A1 for further details).

Next, an algorithm for obtaining coating parameters, for the example that the coating is a paint, using a physical model. The paint parameters may for example include at least one thickness of the paint layer of the coated body, e.g. the total thickness of the paint and/or the paint layer of one or more of its sub-layer(s), and/or other optical material properties.

Figure 9:
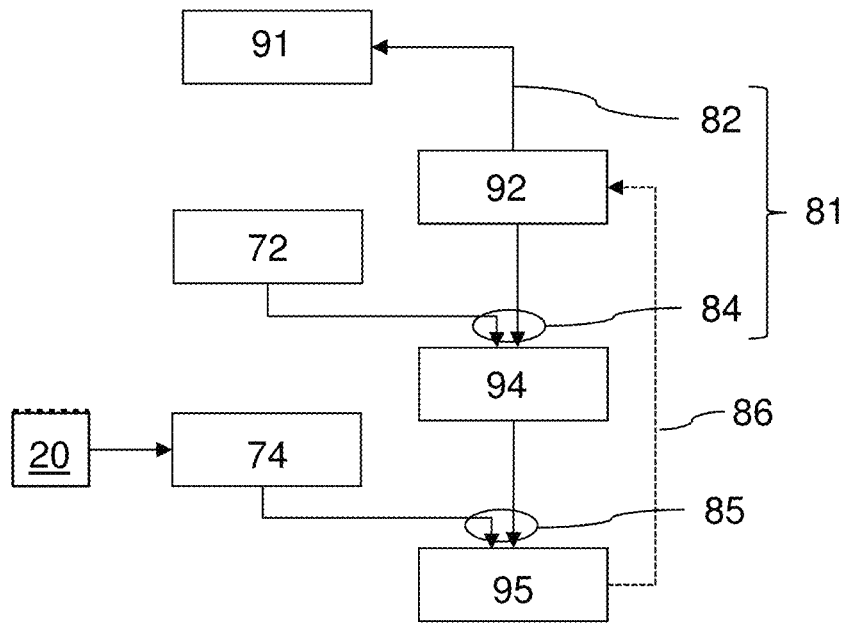
FIG. 9 is a block diagram illustrating a method of characterizing a coated body used in an embodiment of the invention.

This algorithm is illustrated in the block diagram of FIG. 9 in more detail. This algorithm is based on a physical (optical) model 81. The physical model 81 includes a waveform-prediction map 84 that maps the model parameters 92 as input to a predicted waveform 94 as output. Further, the model 81 includes a paint-parameter map 82 that maps the model parameters 92 as input to the paint parameters 91 as output. Herein, the model parameters 92 are, for example, a parameterization of the index of refraction $n(\omega)$ and the thickness d for each layer; and the predicted waveform 94 is, for example, a predicted form of the response signal.

The algorithm further includes an error function 85 that expresses a deviation 95 between the predicted response 94 on the one hand and the reconstructed response 74 (the reconstructed incoming pulse shape of the incoming THz radiation obtained from the THz detector 20 via the pulse shape reconstruction module—not shown in FIG. 9—according to a method of the present invention) on the other hand.

Next, the iterative algorithm itself, as illustrated in FIG. 9, is described in more detail. In a first step, initial fit parameters 92 are generated, e.g. as random numbers or plausible initial values. In this example, as stated above, the fit parameters are given by the respective thickness and parameters characterizing the respective index of refraction of each layer. The model parameters 92 are then iteratively selected such that they minimize the error function 85, i.e., that they provide a best fit to the reconstructed response 74. Then, the final fit parameters 92 are used for calculating the paint parameters 91 (e.g. thicknesses) via the paint-parameter map 82. Further details of the method are described in EP 2899498 A1 and in WO 2016/138935 A1 (description of FIG. 4). The method can in particular be used for determining a dry layer thickness of a dry layer, a wet layer thickness of a wet layer, and/or a predicted dry layer thickness of a wet layer, as described in these references. By improving the accuracy and reliability of the measured pulse shape of the incoming THz pulse as described herein, the reliability and accuracy of the resulting characterization of the coating is further improved.

Next, a paint system and a painting process using the system according to the invention are described with reference to FIG. 10. In the following, the painting of an automobile is described as an example, but the example can be generalized to the coating of other bodies.

Figure 10:
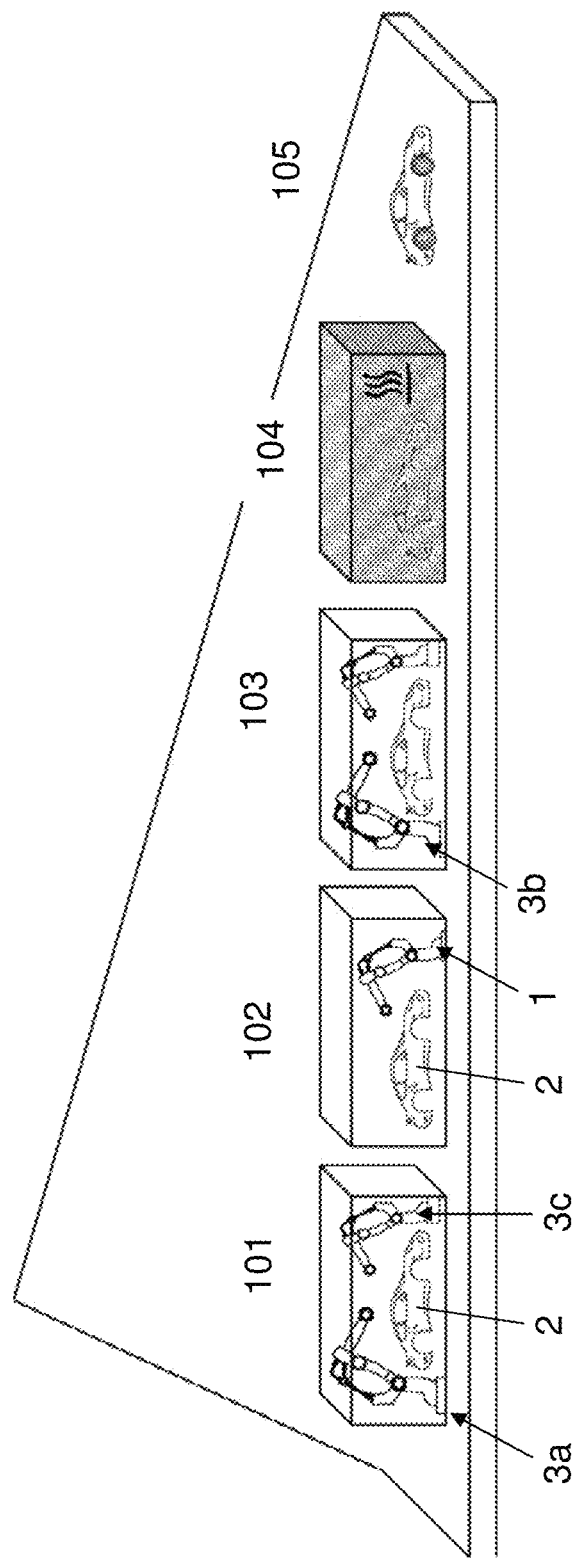
FIG. 10 is a schematic view of a painting facility according to an embodiment of the invention.

FIG. 10 shows a schematic drawing of the paint system being a paint line. The paint line has a number of cubicles for e.g. painting, flash-off, quality control, re-adaptation of the painting and curing, namely a paint booth 101, a cubicle (flash-off zone) 102 for quality control of paint based on THz technology, an (optional) further paint booth 103 for correcting the paint layers, a heated cubicle (furnace) 104 for curing the paint, and an exit 105 towards the next processing step.

The paint system may include further: A transportation mechanism for transporting the coated body 2 from the paint booth 101 through the other cubicles towards the exit 105; climate control in each cubicle; a temperature and humidity sensor in each cubicle; robots which are equipped for at least one of painting the automobile body; being detection apparatus 1 for performing quality control of the painted bodies; or handling robot(s) for carrying the painted bodies.

Next, the individual cubicles and their functionality in the paint system of FIG. 10 are described in more detail. The paint booth 101 has a painting unit (painting robot) 3*a* for applying a paint layer to the body 2. Optionally, more than one paint layer may be applied. A further robot 3*b* is provided for handling the automobile component, e.g. moving it for being painted properly. Subsequently the transportations system moves the body to the flash-off zone 102, at or close to which early quality control based on THz technology is performed.

The flash-off zone 102 has a detection apparatus 1 according to the invention for quality control right after the paint deposition, preferably while the paint is still wet. Thereby, an early observation of possible defects on the painted surface is possible. As described above, the detection apparatus 1 is configured to scan the automobile body with a predefined pattern, such as to obtain quality parameters, such as at least one of the thickness of the wet paint and a prediction of the dry state thickness and information about other possible defects. This information may be mapped onto the entire scanned automobile body surface. Thus, the detection apparatus 1 enables non-contact and non-destructive early quality control of the freshly deposited paint layers on automobile bodies while being processed in the paint line.

If a fault is sensed by the detection apparatus 1, the automobile body 2 can be removed from the main line at an early stage, such that it is ensured that the downstream line only contains bodies which are correctly painted. Moreover, by providing the detection apparatus 1 in the flash-off zone, where the body anyway has to wait for the solvent to partially evaporate, the quality control does not take up any extra time and on the contrary strongly reduces the lead time of the correctly painted bodies by enhancing the efficiency of the main paint line.

Optionally, the automobile body 2 may undergo an additional corrective painting step either in the flash-off zone 102 or, after being transported back, in the paint cubicle 101, or in an optional further paint cubicle 103 (by further painting robot 3*b*). The latter option allows the body 2 to stay in the main line.

The painting process typically involves two to three layers. These layers can be deposited all in one paint booth 101 (wet-on-wet technique), or there can be additional paint booths (not shown) and associated cubicles for each additional layer, either after a flash-off cubicle 102 or after a curing furnace 104. Quality control by the detection apparatus 1 can take place after each paint booth or cubicle or only after a specific one.

Optionally, the paint system may have a close loop feedback control system which receives data from the detection apparatus 1 in cubicle 102 and sends it directly or indirectly to prior equipment in the process line, such as the paint robot 3*a* in cubicle 101. An indirect sending would be provided if the data is sent via another entity which has capability other than mere forwarding of the data, e.g. via a processing unit which calculates the adapted program for the robot. The close loop feedback system influences the process parameters of the paint robot 3*a* depending on the data received from the detection apparatus 1. Alternatively or additionally, the feedback control system may send the data also to later equipment in the process line, such as to paint robot 3*b* in cubicle 103. The close loop feedback system then influences the process parameters of the paint robot 3*b* depending on the data received from the detection apparatus 1.

Thus, the close loop feedback control system can be used in the case that the deviations of the quality parameters resulting from the early quality control are for instance reproducible for several painted bodies 2 and/or seem to be systematic. In these cases the systematic issues can be corrected in a timely manner.

Further alternatives and extensions to the embodiments described herein are possible. Extensions can, for instance, be provided by adding equipment to the system after the early quality control which deals with the consequence of the (negative) outcome.

FIG. 10 suggests an in-line paint booth which immediately corrects the failures of the paint layers in cubicle 103. However, there may also be an alternative route in the system (horizontal but also vertical) which leads the coated body 2 to another zone of the factory and/or which removes the particular coated body from the product line. From such an alternative route, again two options exist: either leaving the corrected automobile bodies on a separate process line, or reentering them onto the main line of FIG. 10.

Although the invention has been mainly described in the context of quality control of paint layers of automobile components, the invention is not restricted to this application. For example, the invention can be adapted to other coated bodies, such as not only an automobile component, but also a train component, an aircraft component, and a wind turbine component, and others. It can also be used for quality control of other materials such as paper sheets or semiconductors.

DESCRIPTION OF GENERAL, OPTIONAL ASPECTS OF THE INVENTION

In the following, some more aspects of the invention are described. Unless explicitly stated otherwise, the aspects are optional and independent of each other so that, for example, any aspect or embodiment described in this document can be combined with any other aspect or embodiment.

First, some aspects relating to the target body are described in more detail. According to one aspect, the target body is a coated body. The coating may be multi-layered having at least a first and a second coating layer. The layers are arranged, in thickness direction of the coated body, on top of one another. According to an aspect, the total number of coating layers is eight or less. According to an aspect, the coating is less than 200 µm thick. According to a further aspect, the coating is a paint film. The paint film may comprise at least one of the following layers (a)-(d): (a) an e-coat layer; (b) a primer layer; (c) a base coat layer; and (d) a clear coat layer.

According to a further aspect, the target body is one of an automobile component, a train component, an aircraft component, and a wind turbine component. According to a further aspect, the target body comprises at least one of a ferrous metal, a non-ferrous metal, and a fiber composite material as a substrate on which a coating layer is applied (optionally with other coating layers in between).

Next, aspects relating to the THz emitter and detector are described. According to an aspect, the THz emitter comprises a THz optical system for directing the emitted THz radiation along a first path from the THz emitter to the target body, interacts with the target body, and travels along a second path from the target body to the THz detector. According to an aspect, the THz emitter is adapted for emitting the THz radiation as a (preferably periodical) time series of THz pulses having an outgoing pulse shape. According to an aspect, the outgoing pulses of a series of outgoing pulses have essentially the same pulse shape. Unless otherwise stated, the pulse shape is understood to be in real-time. For example, the THz emitter may comprise a THz antenna and an activation laser emitting periodically ultrashort laser pulses onto the THz antenna for causing the THz antenna to emit THz pulses.

According to an aspect, the THz detector has a switchably conductive antenna portion, and the detecting of the incoming THz radiation comprises: applying, at different time offsets for respective ones of the incoming THz pulses, a pulsed gating signal to the antenna portion so that the antenna portion becomes conductive; and measuring a pulse portion of the incoming THz pulse while the pulsed gating signal is applied.

According to an aspect, the THz detector comprises a THz radiation receiver and a THz optical system (e.g. one or more lenses) for directing the THz radiation having interacted with the coated body to the THz radiation receiver. The THz detector further comprises a tunable light delaying unit coupling the THz radiation receiver to the laser source used for triggering the THz emitter, so that the THz radiation receiver is enabled to receive the source laser radiation from the laser source for activating the THz detector, with a tunable delay. Thereby, the same laser source radiation received by the THz emitter can also be received by the THz detector. This allows the THz receiver to function in an analogous manner as the THz receiver shown in FIG. 1 of EP 2 213 977 A1, with the important difference that in the present application the system measures a time-of flight quantity and uses the time-of flight quantity for correcting for a variation in the time of flight of the THz radiation.

According to a further aspect, the THz radiation receiver comprises a photonic crystal or an antenna, and/or the THz radiation emitter comprises an antenna or a Cherenkov phase-matched THz generation module, for example. The photonic crystal may comprise, e.g., DAST, GaP, ZnTe; the photoconductive antenna may comprise, e.g., InGaAs or GaAs. According to a further aspect, the THz radiation emitter/receiver is adapted for emitting/receiving the THz radiation signal as periodic THz pulses.

Herein, THz radiation is defined as electromagnetic radiation of (i.e. including a non-negligible signal component having) a frequency in the range of 0.01-10 THz. The lower bound is preferably 0.05 THz and even more preferably 0.1 THz. The detected signal (e.g. time-domain waveform and/or frequency-domain spectrum of the detected THz radiation) is also referred to as the response signal.

Next, some general aspects of the detection head are described. According to an aspect, the detection head comprises the THz emitter and the THz detector and a solid connecting body. The connecting body establishes a mechanically stable connection between the THz emitter and the THz detector. The body may allow a motion between the THz emitter and the THz detector, e.g., by means of an actuator, a joint, and/or a gear, or may be rigid. According to an aspect, the detection head is adapted for a non-contact measurement, i.e. without any sensor component requiring direct physical contact with the coated body. This does not exclude a holder holding the coated body, or any further sensor component other than the THz emitter and receiver having contact with the target body.

Next, some aspects relating to the geometrical arrangement of the detection apparatus are described in more detail. According to an aspect, the THz emitter and the THz detector may be arranged, in an operating state, on the same side of the coated body. This is particularly advantageous in the case that the substrate of the coated body is reflective to the THz radiation, e.g. a metal substrate of an automotive body.

Alternatively, the THz emitter and the THz detector can be arranged for being, in an operational state, on opposite sides of the coated body for performing a transmission measurement. This is particularly useful if the substrate of the coated body is at least partially transparent to THz radiation (e.g. transmission of at least 0.1% of the beam intensity of the THz radiation).

Next, some aspects relating to the sensor are described. The sensor is adapted for measuring a time-of-flight quantity d affecting the time of flight of the THz radiation along at least one of the first path and the second path, preferably along the entire path from the THz emitter to the THz detector. The time-of-flight does not need to be the signal directly measured by the sensor, but may be a derived quantity. The time-of-flight quantity is measured in a time-dependent manner and preferably with a temporal resolution that is equal to or smaller than the period between two subsequent laser pulses and/or than a main vibration period of the target body.

Next, some aspects relating to the operation of the pulse shape reconstruction module are described. According to an aspect, the method comprises synchronizing the time-of-flight quantity d with the (raw) detector data measured by the THz detector. The synchronizing comprises assigning, for each of the incoming THz pulse (or for each of the raw data measurements), a respective time series element of the time-of-flight quantity corresponding to the time of the incoming THz pulse (or of the raw data measurement).

According to an aspect, operation of the pulse shape reconstruction module is adjusted using the time-of-flight quantity d, for correcting for a variation in the time of flight of the THz radiation. For example, the pulse shape reconstruction module may determine a reconstructed incoming pulse shape of the incoming THz radiation, based on the raw detector data and on the synchronized time-of-flight quantity. More specifically, the pulse shape reconstruction module may reconstruct the incoming pulse shape from the measured pulse portions of multiple THz pulses (raw data measured by the THz detector), and from respective time offsets and correction times (time-of-flight quantity) associated to the respective pulse portion. The time offsets are offsets of the measurement time of the THz detector relative to a reference time related to the emitted THz pulse, and the correction times describe (are) variations in the time of flight of the THz pulse, obtained from the sensor output. According to an aspect, the determining of the reconstructed incoming pulse shape comprises adding the correction time for a respective one of the incoming THz pulses to the time offset for the respective incoming THz pulse. Herein, subtracting is also regarded as a form of adding.

According to an aspect, the determining of the reconstructed incoming pulse shape comprises determining, for each of the incoming THz pulses, a correction time, the correction time describing a relative time lag due to the time of flight of the respective incoming THz pulse, wherein the pulse shape reconstruction module determines the correction time based on the measured time-of-flight quantity; and determining a reconstructed incoming pulse shape of the incoming THz radiation, based on the raw detector data and on the correction time.

According to an aspect, the determining of the reconstructed incoming pulse shape comprises calculating, for each incoming THz pulse, a corrected delay time by adding a respective correction time td obtained from the time-of-flight quantity to the respective delay time by which the THz receiver is activated relative to the emitted THz pulse. The correction time td may be obtained as the time-of-flight variation tv of the respective incoming THz pulse. The reconstructed incoming pulse shape of the incoming THz radiation may then be determined based on the raw detector data and the corrected delay time.

According to an aspect, the incoming pulse shape is reconstructed in time domain.

Next, some aspects relating to the processing of the detected response signal are described. The detection apparatus is configured for characterizing a coated body by any method or method steps described herein. Herein, the term "configured for" includes that the processing unit is equipped and programmed to this effect. For this purpose, a memory of the processing unit may be equipped with program code for causing a processor of the processing unit to execute the method according to any aspect described herein. According to a further aspect, the processing unit has a memory containing code therein causing the processor to perform the method steps.

According to an aspect, a method of characterizing the coated body by at least one coating parameter based on fitting to a physical model is provided. The method comprises: emitting, by the THz emitter, a THz radiation signal towards the coated body such that the THz radiation interacts with the polymeric coating; detecting, by the THz detector, a response signal being the detected THz radiation signal having interacted with the polymeric coating; determining, by the processing unit, model parameters of the physical model by optimizing the model parameters such that a predicted response signal of the physical model is fitted to the detected response signal, the model parameters being indicative of optical material properties of the polymeric coating describing the interaction of the THz radiation signal with the polymeric coating; and determining, from the determined model parameters, at least one coating parameter. The at least one coating parameter may include a thickness of the polymeric coating and/or other parameters described herein.

Next, some aspects relating to the method and facility for painting a body are discussed. According to an aspect, the painting facility comprises a painting unit for applying a paint layer to the body (e.g. a paint spraying unit/robot for applying a water-borne paint or a solvent-borne paint); and a sensing unit comprising the detection apparatus described herein. The painting facility may be a paint line of an automobile factory. The painting unit and the sensor unit may be provided in a single paint booth, which allows for immediate quality control of the paint layer. Alternatively, the painting unit and the sensor unit may be provided in different booths, which allows for quality control of the paint layer, e.g., during or after flash-off and/or curing.

According to an aspect, the detection apparatus is adapted for characterizing the wet paint layer while the body is still being painted and/or while the wet paint layer has not yet finished the drying process. Optionally, the detection apparatus is operationally coupled to the painting unit for further processing the coated body in dependence of the characterized wet paint layer, e.g. of the obtained coating parameters. For example, the painting unit may be configured for adapting painting parameters in response to the coating parameters. Alternatively, the detection apparatus is operationally coupled to a further painting unit for further processing the coated body in dependence of the characterized wet paint layer. The further processing may include removing the coated body from the processing line temporarily (e.g. for re-painting) or permanently. The further processing may also include removing the paint and/or applying further layer(s) of paint, preferably while the wet paint layer is not yet dry.

Aspects of the invention allow quality control of painted bodies, e.g., automobile components, while they are being processed. This allows early quality control while the painted surfaces are still wet, and correspondingly early separation between correctly painted bodies and ones with defects. Due to the early separation, the process lead time can be decreased and parameters of the painting process can be adapted in short time. The detection apparatus and quality control method can be used for on-line, in-line, at-line and off-line quality control, but is preferred to be used in-line.

The system according to the invention is especially applicable in the case that the coating is a paint film having one or more layers of wet paint layer. One use of the system is for the analysis/painting of a painted automobile body or a painted automobile component. Another use is for the analysis/painting of a train body/component, an aircraft body/component such as an aircraft fuselage, aircraft wing, or the like. Another use is for the analysis/painting of a wind turbine component, in particular of a painted blade of a wind turbine. The substrate body may comprise at least one of a ferrous metal, a non-ferrous metal, and a fiber composite material. For example, an application of the present aspect of the invention is defect detection in blades of wind turbines e.g. for off-shore purposes. Here, the coated body is a wind turbine blade containing a defect below the wet paint layer.

Next, some aspects relating to digital technology and network integration are discussed. According to an aspect, the detection apparatus may further comprise a network interface for connecting the device to a data network, in particular a global data network. The data network may be a TCP/IP network such as Internet. The detection apparatus, and in particular its controller, may be operatively connected to the network interface for carrying out commands received from the data network. The commands may include a control command for controlling the device to carry out a task such as starting, stopping and/or controlling a detection run. In this case, the device and/or controller is adapted for carrying out the task in response to the control command. The commands may include a data request. In response to the data request, or without prior request, the apparatus may be adapted for sending measurement information (e.g. a measurement report including the reconstructed incoming pulse shape and/or determined physical properties of the target body) to the network interface, and the network interface is then adapted for sending the measurement information over the network. The measurement information is preferably sent over the network as digital information. The commands may include an update command including update data. In this case, the device and/or controller is adapted for initiating an update in response to the update command and using the update data. Thus, the apparatus may be partially or fully accessible over the network.

The data network may be an Ethernet network using TCP/IP such as LAN, WAN or Internet. The data network may comprise distributed storage units such as Cloud. Depending on the application, the Cloud can be in form of public, private, hybrid or community Cloud.

While the foregoing is directed to embodiments, other and further embodiments may be devised without departing from the basic scope determined by the claims.

We claim:

1. A method for detecting a pulsed THz beam, the method comprising:
   emitting, by a THz emitter, THz radiation comprising a time series of THz pulses having an outgoing pulse shape, so that the THz radiation travels along a first path from the THz emitter to a target body to be inspected, interacts with the target body, and travels along a second path from the target body to a THz detector;
   detecting, by the THz detector, the incoming THz radiation being a time series of incoming THz pulses, and outputting, by the THz detector, a raw detector data being a time series of data relating to an incoming pulse shape of the incoming THz pulses; and
   determining, by a pulse shape reconstruction module, a reconstructed incoming pulse shape of the incoming THz radiation based on the raw detector data,
   wherein the method further comprises:
   measuring, by a sensor, a time-of-flight quantity (d) affecting the time of flight of the THz radiation along at least one of the first path and the second path, the time-of-flight quantity (d) being measured in a time-dependent manner while the THz radiation is emitted by the THz emitter; and
   adjusting operation of at least one of the THz emitter, the THz detector and the pulse shape reconstruction module using the time-of-flight quantity (d), for correcting for a variation in the time of flight of the THz radiation.

2. The method of detecting a pulsed THz beam according to claim 1, wherein the operation of the pulse shape reconstruction module is adjusted by at least one of the following (i) to (iii):
   (i) synchronizing the time-of-flight quantity (d) with the raw detector data;
   (ii) determining, by the pulse shape reconstruction module, a reconstructed incoming pulse shape of the incoming THz radiation, based on the raw detector data and on the, preferably synchronized, time-of-flight quantity; and
   (iii) determining, by the pulse shape reconstruction module, a reconstructed incoming pulse shape of the incoming THz radiation by reconstructing the incoming pulse shape from the measured pulse portions, and from the respective time offsets and correction times associated to the respective pulse portion.

3. The method of detecting a pulsed THz beam according to claim 1, wherein the operation of the THz emitter is adjusted by adapting emission time offsets of the emitted THz pulses in dependence of the time-of-flight quantity (d).

4. The method of detecting a pulsed THz beam according to claim 1, wherein the operation of the THz detector is adjusted by adapting detection time offsets of for detecting portions of the incoming THz pulses in dependence of the time-of-flight quantity (d).

5. The method of detecting a pulsed THz beam according to claim 1, wherein the time-of-flight quantity (d) is a correction time indicating a variation of the time of flight of a respective incoming THz pulse, and wherein the method further comprises calculating the correction time from the time-of-flight quantity (d).

6. The method of detecting a pulsed THz beam according to claim 5, wherein the THz detector has a switchably conductive antenna portion, and wherein detecting of the incoming THz radiation comprises:
   applying, at different time offsets for respective ones of the incoming THz pulses, a pulsed gating signal to the antenna portion so that the antenna portion becomes conductive; and
   measuring a pulse portion of the incoming THz pulse while the pulsed gating signal is applied.

7. The method of detecting a pulsed THz beam according to claim 6, wherein the determining of the reconstructed incoming pulse shape further comprises adding the correction time for a respective one of the incoming THz pulses to the time offset for the respective incoming THz pulse.

8. The method of detecting a pulsed THz beam according to claim 1, wherein the method further comprises determining physical properties of the target body based on the outgoing pulse shape and on the reconstructed incoming pulse shape.

9. The method of coating a target body using the method of detecting a pulsed THz beam according to claim 1, the method of coating the target body comprising:
   applying a coat layer to a target body;
   detecting the pulsed THz; and
   characterizing a coating (2b) of the coat layer applied on the target body (2) including the applied coat layer in a non-contact manner by analyzing the reconstructed incoming THz pulse shape of the incoming THz radiation.

10. The method of coating a target body according to claim 9, wherein the coating (2b) is characterized while the coat layer is a wet coat layer having not yet finished a drying process.

11. An apparatus for detecting a pulsed THz beam, comprising:
   a THz emitter operating to emit THz radiation comprising a time series of THz pulses having an outgoing pulse shape, wherein the THz emitter is configured to be directed towards a target body to be inspected so that the THz radiation travels along a first path from the THz emitter to the target body to be inspected;
   a THz detector operating to detect incoming THz radiation being a time series of incoming THz pulses generated by the emitted THz radiation having interacted with the target body and having travelled along a second path from the target body to the THz detector, and to output a raw detector data being a time series of data relating to an incoming pulse shape of the incoming THz pulses;

a pulse shape reconstruction module operating to synchronize the time-of-flight quantity with the raw detector data, and to determine a reconstructed incoming pulse shape of the incoming THz radiation based on the raw detector data;

a sensor disposed to measure a time-of-flight quantity (d) affecting the time of flight of the THz radiation along at least one of the first path and the second path, the sensor measuring time-of-flight quantity (d) in a time-dependent manner while the THz radiation is emitted by the THz emitter;

wherein at least one of the THz emitter, the THz detector and the pulse shape reconstruction module having an interface for receiving the time-of-flight quantity (d) and being configured for correcting for a variation in the time of flight of the THz radiation using the received time-of-flight quantity (d).

12. The apparatus according to claim 11, further comprising a THz emitter-detector head, wherein the THz emitter and the THz detector are disposed in connection with the THz emitter-detector head mechanically coupling the THz emitter and the THz detector to each other, and wherein at least a sensor portion of the sensor is mechanically coupled to the THz emitter-detector head.

13. The apparatus according to claim 11, wherein at least a sensor portion of the sensor is mechanically coupled (i) to the THz emitter and/or the THz detector, or (ii) to the target body (2), or (iii) to both (i) and (ii).

14. The apparatus according to claim 11, wherein the sensor (80) comprises at least one of the following:
a distance sensor such as an optical distance sensor;
an acceleration sensor;
a vibration sensor;
an ambient air sensor;
an air humidity sensor; and
an optical time-of-flight sensor.

15. The apparatus according to claim 11, further comprising a network interface for connecting the apparatus or one of its parts to a data network, wherein the apparatus is operatively connected to the network interface for sending at least one of the reconstructed incoming pulse shape, determined physical properties of the target body, and device status information as digital information to the data network, wherein the network interface is preferably configured to transceive digital signal/data between the apparatus and the data network, wherein the digital signal/data include operational command and/or information about the apparatus or the network.

16. A coating facility for coating a target body, the coating facility comprising:
a coating unit for applying a coat layer to the target body;
a THz emitter operating to emit THz radiation comprising a time series of THz pulses having an outgoing pulse shape, wherein the THz emitter is configured to be directed towards the target body so that the THz radiation travels along a first path from the THz emitter to the target body;
a THz detector operating to detect incoming THz radiation being a time series of incoming THz pulses generated by the emitted THz radiation having interacted with the target body and having travelled along a second path from the target body to the THz detector, and to output a raw detector data being a time series of data relating to an incoming pulse shape of the incoming THz pulses;
a pulse shape reconstruction module operating to synchronize the time-of-flight quantity with the raw detector data, and to determine a reconstructed incoming pulse shape of the incoming THz radiation based on the raw detector data;
a sensor disposed to measure a time-of-flight quantity (d) affecting the time of flight of the THz radiation along at least one of the first path and the second path, the sensor measuring time-of-flight quantity (d) in a time-dependent manner while the THz radiation is emitted by the THz emitter;
wherein at least one of the THz emitter, the THz detector and the pulse shape reconstruction module having an interface for receiving the time-of-flight quantity (d) and being configured for correcting for a variation in the time of flight of the THz radiation using the received time-of-flight quantity (d) an apparatus according to claim 11; and
an evaluating unit configured to characterize a coating (2b) of the target body (2) including the applied coat layer in a non-contact manner by analyzing the reconstructed incoming THz pulse shape of the incoming THz radiation.

* * * * *